United States Patent
Huiku

(10) Patent No.: US 8,412,296 B2
(45) Date of Patent: *Apr. 2, 2013

(54) NON-INVASIVE DETERMINATION OF THE CONCENTRATION OF A BLOOD SUBSTANCE

(75) Inventor: Matti Huiku, Espoo (FI)

(73) Assignee: General Electric Company, Schenectady, NY (US)

( * ) Notice: Subject to any disclaimer, the term of this patent is extended or adjusted under 35 U.S.C. 154(b) by 1655 days.

This patent is subject to a terminal disclaimer.

(21) Appl. No.: 11/780,525

(22) Filed: Jul. 20, 2007

(65) Prior Publication Data

US 2009/0024011 A1    Jan. 22, 2009

(51) Int. Cl.
*A61B 5/1455* (2006.01)
(52) U.S. Cl. .......................... 600/323; 600/310; 600/322
(58) Field of Classification Search ........... 600/309–344
See application file for complete search history.

(56) References Cited

U.S. PATENT DOCUMENTS

| | | | |
|---|---|---|---|
| 4,714,341 A * | 12/1987 | Hamaguri et al. ............. | 356/41 |
| 4,765,340 A * | 8/1988 | Sakai et al. .................. | 600/324 |
| 4,776,340 A * | 10/1988 | Moran et al. ................. | 600/327 |
| 5,131,391 A * | 7/1992 | Sakai et al. .................. | 600/334 |
| 5,203,329 A * | 4/1993 | Takatani et al. .............. | 600/334 |
| 5,372,136 A | 12/1994 | Steuer | |
| 5,431,170 A * | 7/1995 | Mathews ...................... | 600/479 |
| 6,104,938 A | 8/2000 | Huiku et al. | |
| 6,400,972 B1 | 6/2002 | Fine | |
| 6,501,974 B2 | 12/2002 | Huiku | |
| 6,587,704 B1 | 7/2003 | Fine et al. | |
| 6,671,528 B2 | 12/2003 | Steuer et al. | |
| 6,711,424 B1 | 3/2004 | Fine et al. | |
| 6,873,865 B2 | 3/2005 | Steuer et al. | |
| 7,029,628 B2 | 4/2006 | Tam et al. | |

* cited by examiner

*Primary Examiner* — Eric Winakur
*Assistant Examiner* — Marjan Fardanesh
(74) *Attorney, Agent, or Firm* — Andrus, Sceales, Starke & Sawall, LLP

(57) ABSTRACT

In order to provide a non-invasive and continuous concentration measurement with the technology of standard pulse oximeters, an a priori relationship is created, through an in-vivo tissue model including a nominal estimate of a tissue parameter indicative of the concentration of a blood substance. The a priori relationship is indicative of the effect of tissue on in-vivo measurement signals at a plurality of wavelengths, the in-vivo measurement signals being indicative of absorption caused by pulsed arterial blood. In-vivo measurement signals are acquired from in-vivo tissue at the plurality of wavelengths and a specific value of the tissue parameter is determined based on the a priori relationship, the specific value being such that it yields the effect of the in-vivo tissue on the in-vivo measurement signals consistent for the plurality of wavelengths. The specific value then represents the concentration of the substance in the blood.

18 Claims, 7 Drawing Sheets

NON-INVASIVE DETERMINATION OF THE CONCENTRATION OF A BLOOD SUBSTANCE

FIELD OF THE INVENTION

The present invention relates generally to the determination of the concentration of a substance in the blood of a subject. In a typical application, the invention is employed to determine the concentration of total hemoglobin (THb).

BACKGROUND OF THE INVENTION

Traditionally, hemoglobin measurements have been carried out based on in-vitro analysis of subject's blood. Measurement devices known as co-oximeters determine hemoglobin concentration from a blood sample by measuring spectral light transmission/absorption through a hemolysed blood sample at several wavelengths typically between 500 and 650 nm. An example of a portable co-oximeter is presented in U.S. Pat. No. 7,029,628.

A major drawback related to co-oximeters is that the measurements are invasive, i.e. require a blood sample to be taken from the patient. Furthermore, the co-oximeters are rather expensive laboratory devices and require frequent service and maintenance.

Non-invasive optical hemoglobin measurements in-vivo are based on artificially induced changes in the blood flow of the patient.

U.S. Pat. Nos. 6,400,972, 6,711,424, and 6,587,704 disclose measurement devices based on a so-called occlusion-release (OR) measuring technique. A typical OR based measurement device utilizes a ring-shaped cuff applied to the patient's finger. The device is further provided with a pressurizing arrangement to produce a state of temporary blood flow cessation in the finger by applying an over-systolic pressure and a state of transitional blood flow by releasing the over-systolic pressure. Measurement sessions are carried out during various states of blood flow and the blood absorption characteristics during the said states are analyzed to determine the concentration of a blood constituent, such as hemoglobin.

U.S. Pat. Nos. 5,372,136, 6,671,528 B2, and 6,873,865 B2 disclose measurement devices in which the artificially induced changes in the blood flow are combined with light transmission/absorption measurements at two or more wavelengths. The wavelengths include an isobestic wavelength (805 nm) and a wavelength at which water absorption is high (1310 nm or 1550 nm) to detect the concentrations of hemoglobin and water, respectively.

Compared to invasive techniques, non-invasive optical hemoglobin or hematocrit measurements have clear advantages, which include the elimination of both painful blood sampling and the risk of infection. Furthermore, non-invasive measurements are simpler to carry out and require less training of the nursing staff.

However, there are also several drawbacks related to the above non-invasive techniques. First, the devices are rather complicated since the optical measurement involves synchronized operation of the optical and pneumatic components of the measurement device. Second, the measurement cannot be carried continuously, but requires a certain measurement period for each measurement. Typically, the measurement cycle is manually initiated, which makes the devices suitable for spot checks after the need for the hemoglobin measurement has been recognized based on subject's symptoms. Consequently, the current non-invasive hemoglobin meters cannot be used for alarming of a sudden hemoglobin loss. Third, normal low-cost silicon detectors, which are used in standard pulse oximeters, can be used only in the near infrared region, since their response ends at a wavelength of about 1000 nm. Therefore, more expensive detector technology must be used for enabling measurement of water absorption in the short-wavelength infrared region, such as at wavelengths around 1300 nm.

The present invention seeks to eliminate the above drawbacks and to bring about a novel mechanism for non-invasive and continuous determination of the concentration of a blood substance, such as hemoglobin.

SUMMARY OF THE INVENTION

The present invention seeks to provide a novel non-invasive mechanism for determining the concentration of a desired substance, such as hemoglobin, in the blood of a subject. The present invention further seeks to provide a non-invasive measurement mechanism that allows continuous concentration measurement to be performed with the technology of standard pulse oximeters.

In the present invention, a theoretical relationship is formed, which is indicative of the effect of tissue on in-vivo measurement signals at the wavelengths of the apparatus. The in-vivo measurement signals are then measured from in-vivo tissue at different wavelengths of the apparatus. The concentration of the substance in the blood may be determined based on the theoretical relationship by requiring that the effect of the in-vivo tissue on the in-vivo signals is consistent for all wavelengths at which the in-vivo measurement is performed. The theoretical relationship may be utilized to find out consistency. The present invention thus provides a tissue model assisted method that evaluates the effect of the in-vivo tissue on the measurement signal, which is indicative of the absorption caused by pulsed arterial blood. The pulsed arterial blood thus serves as a marker that must be measured in a consistent manner for the plurality of wavelengths.

Thus one aspect of the invention is providing a method for determining the concentration of a substance in the blood of a subject. The method comprises creating, through an in-vivo tissue model including a nominal estimate of a tissue parameter indicative of the concentration of a blood substance, an a priori relationship indicative of the effect of tissue on in-vivo measurement signals at a plurality of wavelengths, wherein the in-vivo measurement signals are indicative of absorption caused by pulsed arterial blood. The method further comprises acquiring the in-vivo measurement signals from in-vivo tissue at the plurality of wavelengths and determining, based on the a priori relationship, a specific value of the tissue parameter for which the effect of the in-vivo tissue on in-vivo measurement signals is consistent for the plurality of wavelengths, the specific value representing the concentration of the substance.

In order to find out when consistency occurs, a predetermined parameter may be employed, which is indicative of the said effect at the different wavelengths. At least one, but typically a set of parameter estimates is calculated for the predetermined parameter based on the measured signals in-vivo. The set of estimated parameter values is compared with an equivalent set of parameter values calculated within the theoretical tissue model, i.e. based on the theoretical relationship. Consistency is searched for between the said in-vivo parameter estimates and their theoretical equivalents within the tissue model. The values of the tissue parameters that render the values of the predetermined parameter as consistent as possible, determine the concentration of the substance in blood. Different parameters may be utilized as the predetermined parameter, and the criterion of consistency depends on the parameter used.

Another aspect of the invention is that of providing an arrangement for determining the concentration of a substance in the blood of a subject. The arrangement comprises a first determination unit configured to create, through an in-vivo tissue model including a nominal estimate of a tissue parameter indicative of the concentration of a blood substance, an a priori relationship indicative of the effect of tissue on in-vivo measurement signals at a plurality of wavelengths, wherein the in-vivo measurement signals are indicative of absorption caused by pulsed arterial blood. The arrangement further comprises a measurement unit configured to acquire the in-vivo measurement signals from in-vivo tissue at the plurality of wavelengths and a second determination unit configured to determine, based on the a priori relationship, a specific value of the tissue parameter for which the effect of the in-vivo tissue on in-vivo measurement signals is consistent for the plurality of wavelengths, the specific value representing the concentration of the substance.

Since the concentration measurement of the invention rests on a conventional $SpO_2$ measurement, the only instrument needed is a pulse oximeter employing multiple, at least three, wavelengths. Furthermore, any additional hardware, such as an arrangement for controlling the blood flow of the subject, is not required. The cost-efficiency is further enhanced by the fact that the entire measurement can be made at wavelengths allowing the use of low-cost silicon detectors, i.e. the more expensive detector technology necessary in the short-wavelength infrared region is not required. The measurement is also easy to perform and may be carried out continuously. The measurement and apparatus is thus suitable to diagnostics and monitoring of substance concentration at various locations, such as hospitals, doctor's offices, and homes.

The present invention thus allows automatic and continuous evaluation of the concentration of a blood substance to be introduced in clinical set-ups and in self-care devices in a cost-effective way.

A further aspect of the invention is that of providing a sensor for determining the concentration of a substance in the blood of a subject. The sensor comprises an emitter unit configured to emit radiation through the tissue of the subject at at least three wavelengths, a detector unit configured receive the radiation and to produce in-vivo measurement signals for the at least three wavelengths, wherein the in-vivo measurement signals are indicative of absorption caused by pulsed arterial blood of the subject and a first memory unit configured to store an a priori relationship indicative of an estimated effect of the tissue on in-vivo measurement signals at the at least three wavelengths, the a priori relationship being created through an in-vivo tissue model including a nominal estimate of a tissue parameter indicative of the concentration of a blood substance.

Still further aspects of the invention are those of providing a memory unit storing the a priori relationship and a computer program product for determining the concentration of a substance in the blood of a subject. The computer program product comprises a first program product portion configured to receive the a priori relationship indicative of the effect of tissue on in-vivo measurement signals at a plurality of wavelengths, a second program product portion configured to receive in-vivo measurement signals acquired from in-vivo tissue at the plurality of wavelengths, and a third program product portion configured to determine, based on the a priori relationship, a specific value of the tissue parameter for which the effect of the in-vivo tissue on in-vivo measurement signals is consistent for the plurality of wavelengths, the specific value representing the concentration of the substance.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 9 in the appended drawings, wherein.

DETAILED DESCRIPTION OF THE INVENTION

A pulse oximeter comprises a computerized measuring unit and a probe attached to the patient, typically to a finger or ear lobe. The probe includes a light source for sending an optical signal through the tissue and a photo detector for receiving the signal transmitted through or reflected from the tissue. On the basis of the transmitted and received signals, light absorption by the tissue may be determined. During each cardiac cycle, light absorption by the tissue varies cyclically. During the diastolic phase, absorption is caused by venous blood, non-pulsating arterial blood, cells and fluids in tissue, bone, and pigments, whereas during the systolic phase there is an increase in absorption, which is caused by the inflow of arterial blood into the tissue part on which the sensor is attached. Pulse oximeters focus the measurement on this pulsating arterial blood portion by determining the difference between the peak absorption during the systolic phase and the background absorption during the diastolic phase. Pulse oximetry is thus based on the assumption that the pulsatile component of the absorption is due to arterial blood only.

In order to distinguish between two species of hemoglobin, oxyhemoglobin ($HbO_2$), and deoxyhemoglobin (RHb), absorption must be measured at two different wavelengths, i.e. the probe of a traditional pulse oximeter includes two different light emitting diodes (LEDs) or lasers. The wavelength values widely used are 660 nm (red) and 940 nm (infrared), since the said two species of hemoglobin have substantially different absorption at these wavelengths. Each LED is illuminated in turn at a frequency which is typically several hundred Hz.

Figure 1:
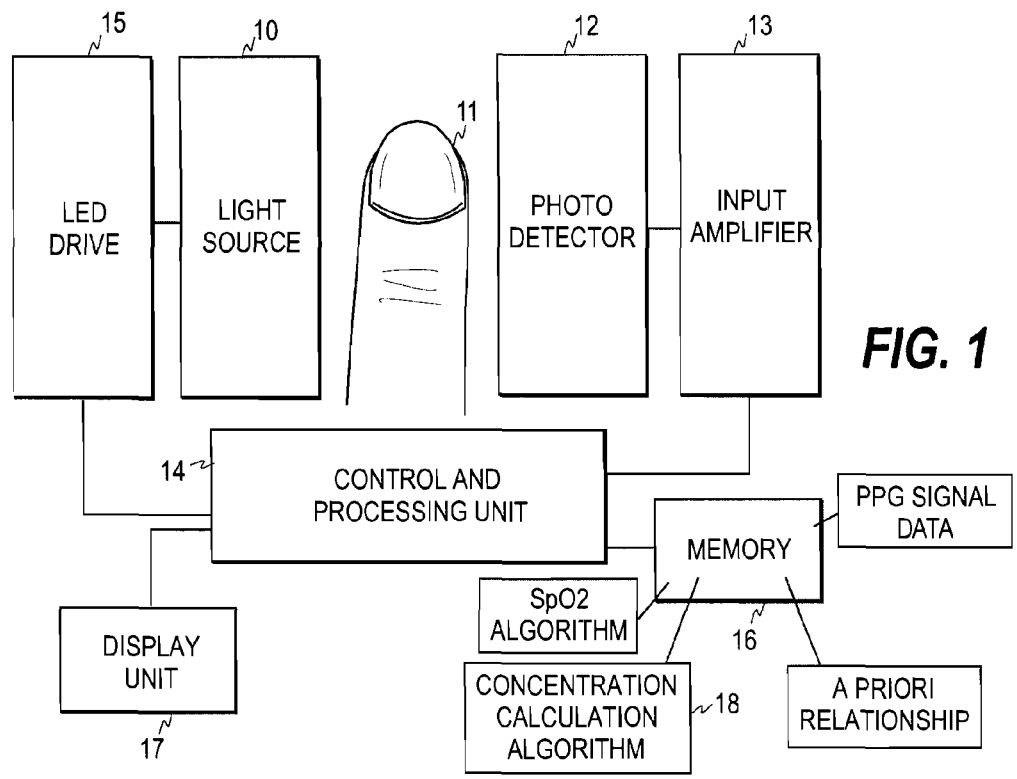
FIG. 1 is a block diagram illustrating one embodiment of a pulse oximeter according to the invention.

FIG. 1 is a block diagram of one embodiment of a pulse oximeter according to the invention. Light transmitted from a light source 10 including a plurality of LEDs or lasers passes into patient tissue, such as a finger 11. As discussed below, the number of wavelengths used may vary according to the embodiment of the invention. However, at least two LEDs (wavelengths) are required for oxygen saturation measurement.

The light propagated through or reflected from the tissue is received by a photodetector 12, which converts the optical signal received at each wavelength into an electrical signal pulse train and feeds it to an input amplifier 13. The amplified signal is then supplied to a control and processing unit 14, which converts the signals into digitized format for each wavelength channel. The digitized signal data is then utilized by an $SpO_2$ algorithm. The control and processing unit executes the algorithm and drives a display 17 to present the results on the screen of the display. The $SpO_2$ algorithm may be stored in a memory 16 of the control and processing unit.

The control and processing unit further controls a source drive 15 to alternately activate the LEDs. As mentioned above, each LED is typically illuminated several hundred times per second. The digitized photoplethysmographic (PPG) signal data at each wavelength may also be stored in the said memory before being supplied to the $SpO_2$ algorithm.

With each LED is illuminated at such a high rate as compared to the pulse rate of the patient, the control and processing unit obtains a high number of samples at each wavelength for each cardiac cycle of the patient. The value of these samples varies according to the cardiac cycle of the patient, the variation being caused by the arterial blood, as is shown below in FIG. 2.

In order for variations in extrinsic factors, such as the brightness of the LEDs, sensitivity of the detector, or thickness of the finger, to have no effect on the measurement, each signal received is normalized by extracting the AC component oscillating at the cardiac rhythm of the patient, and then dividing the AC component by the DC component of the light transmission or reflection. The signal thus obtained is independent of the above-mentioned extrinsic factors.

In the present invention, a conventional pulse oximeter of the above type is upgraded with a mechanism for determining the concentration of a desired substance, such as hemoglobin, in the blood of a subject. For this purpose, a calculation algorithm 18 may be stored in the memory of the pulse oximeter. The control unit executes the algorithm which may utilize the same digitized signal data as the $SpO_2$ algorithm or the results derived in the $SpO_2$ algorithm. As discussed below, as compared to a standard two-wavelength pulse oximeter, the pulse oximeter of the invention is further provided with extra wavelengths and a dedicated sensor, for example. However, the operation of the concentration calculation algorithm is discussed first by using hemoglobin as an example of the blood substance.

Figure 2:
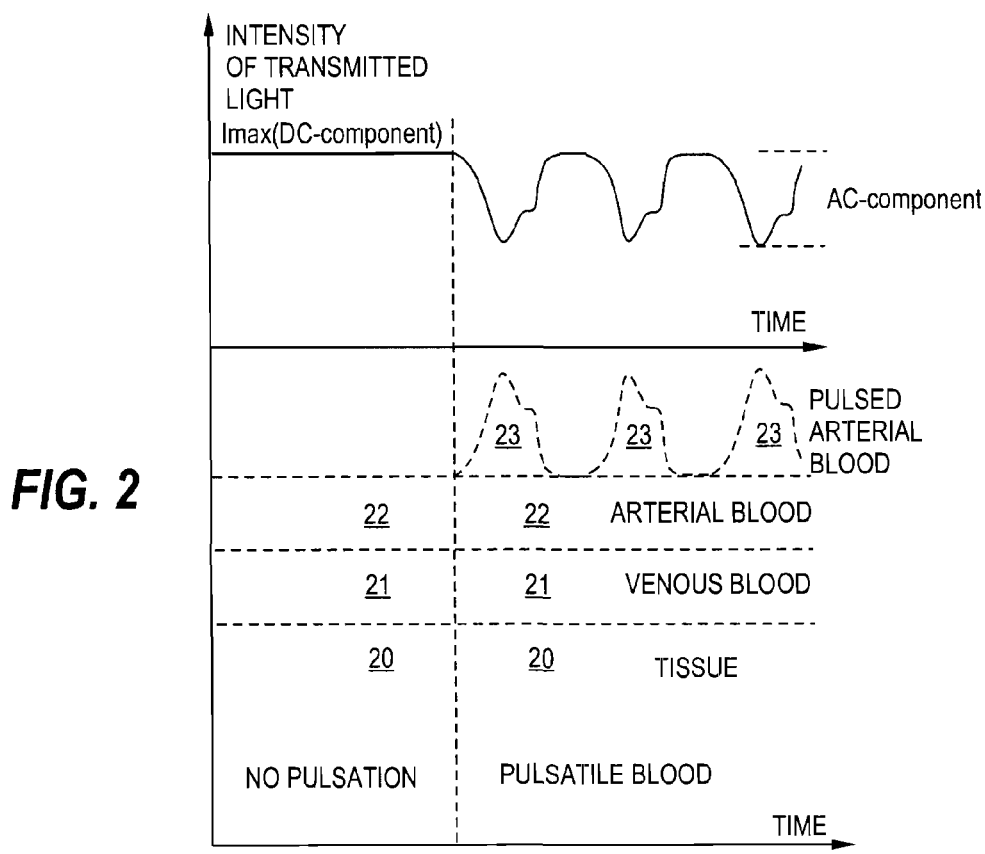
FIG. 2 illustrates a simple model based on the Lambert-Beer theory of pulse oximetry.
Figure 3:
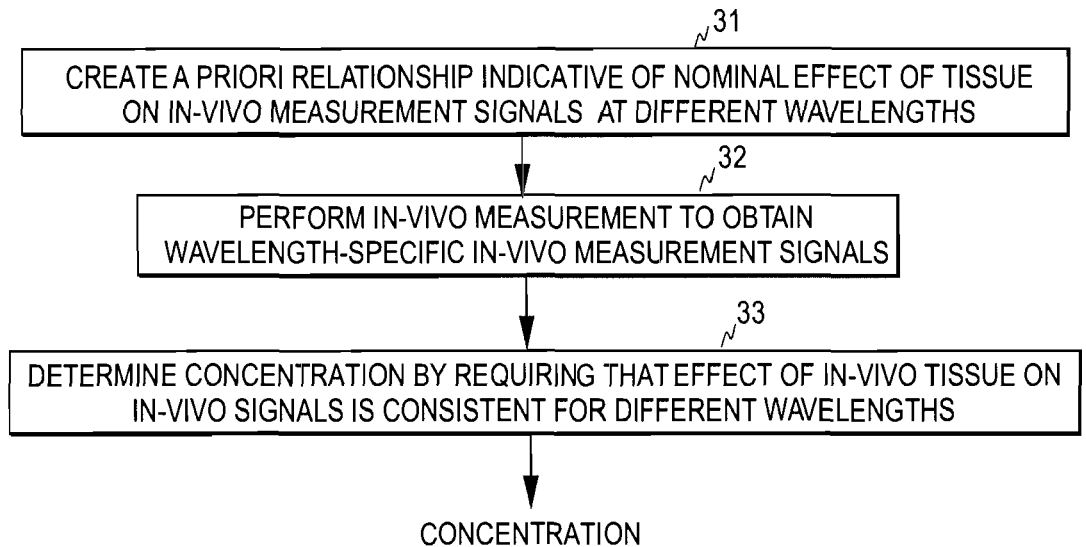
FIG. 3 is a flow diagram illustrating the concentration determination of the invention.

FIGS. 2 and 3 illustrate the general principle of the measurement of the invention. FIG. 2 illustrates the Lambert-Beer tissue model and how the intensity of light transmitted through a finger, for example, varies according to blood pulsation. FIG. 3 in turn illustrates the basic steps of the invention.

The determination of the hemoglobin is based on a relationship between the in-vivo measured PPG signals and wavelength-specific values of a predetermined parameter indicative of the wavelength-dependent effect of the in-vivo tissue on the measured signal and thus also on the consistency of the effect at different wavelengths. The relationship defines how values may be derived for the predetermined parameter from the in-vivo signals.

In-vivo based values of the predetermined parameter are examined to find out when consistency occurs for the wavelengths at which the in-vivo measurement is made. One tissue model that may be utilized in this context is a model based on the known Lambert-Beer theory. FIG. 2 illustrates a simple model for the Lambert-Beer (L-B) theory of pulse oximetry. The theory is based on a multilayer model in which light absorption is caused by different tissue compartments or layers stacked on each other. As illustrated in the figure, the tissue compartments include the actual tissue layer 20, layers of venous and arterial blood, 21 and 22, and the layer of pulsed arterial blood 23. The model assumes that the layers do not interact with each other and that each layer obeys the ideal L-B model, in which light scattering is omitted. The ideal signal measured by a pulse oximeter in the L-B model is thus the signal that is left when the absorption caused by each layer is deducted from the input light signal. The total absorption may thus be regarded as the total absorption caused by the actual tissue, venous blood, arterial blood, and pulsed arterial blood.

In the present invention, however, an in-vivo tissue model is used, which includes a tissue parameter representing the concentration of a desired blood substance, such as hemoglobin. The in-vivo tissue model is such that it adds interactions between the ideal L-B layers, i.e. in the model the in-vivo signals are affected by the absorbing and scattering tissue components specified in the L-B tissue model for layers 20-23. The three layers 20-22 beneath the pulsed arterial blood are in this context termed the background, since they form a "background" for the pulsatile component of the absorption (i.e. for the measurement signal).

FIG. 3 illustrates the basic steps of the invention. In the present invention, an a priori relationship is thus formed, which is indicative of the (nominal) effect of the tissue on in-vivo measurement signals at the wavelengths of the apparatus (step 31). The nominal condition represents the normal concentrations of a substance in blood for a typical population of subjects. The in-vivo measurement signals are then measured from in-vivo tissue at different wavelengths (step 32). The concentration of the substance in the blood may be determined based on the a priori relationship by requiring that the effect of the in-vivo tissue on the in-vivo signals remains consistent for all wavelengths at which the in-vivo measurement is performed (step 33). Consistency may be found based on the a priori relationship.

The a priori relationship created is based on the above-mentioned in-vivo tissue model obtained by adding interactions to a known model, such as the Lambert-Beer model. The tissue model obtained typically includes a number of parameters, one of the parameters being the above-mentioned tissue parameter, i.e. a parameter which is indicative of the concentration of a desired blood substance, such as hemoglobin. The a priori relationship may be created with nominal tissue parameter values and the relationship may describe the effect of the tissue on a predetermined parameter derivable from the in-vivo signals, wherein the parameter is such that the effect, which is wavelength-dependent, may be seen in it. As discussed below, the predetermined parameter derivable from the in-vivo signals may be such that background color and/or color density is/are reflected in the value of the parameter.

Consistency is detected based on the predetermined parameter and the a priori relationship. However, the criterion indicating the occurrence of consistency depends on the predetermined parameter utilized. In one embodiment of the invention, a theoretical value for the predetermined parameter is determined. This theoretical value may be calculated using an ideal tissue, such as only the pulsating arterial blood in the L-B model. An in-vivo measurement is then performed (step 32) and based on the measurement at least one in-vivo based value is determined for the predetermined parameter. However, typically several wavelength-specific in-vivo based values are determined. The a priori relationship is then altered by adjusting the value of the tissue parameter so that it yields the best possible agreement between the in-vivo based values and the theoretical values of the predetermined parameter, i.e. the value of the tissue parameter is searched for, for which the in-vivo based values and the theoretical equivalent(s) correspond to each other. This value of the tissue parameter is regarded as the actual concentration of the blood substance.

The above theoretical a priori relationship is created in the manufacturing phase of the apparatus and stored in the memory of the apparatus. In connection with an in-vivo measurement, the apparatus may then determine, based on the relationship and in-vivo measurement signals, a set of wavelength-specific values for the predetermined parameter. The consistency of the wavelength-specific values is checked based on the a priori relationship and if consistency is not found directly, the a priori relationship is adjusted so that the set of wavelength-specific values indicate consistency. The value of the tissue parameter that yields the consistency determines the concentration.

Figure 4:
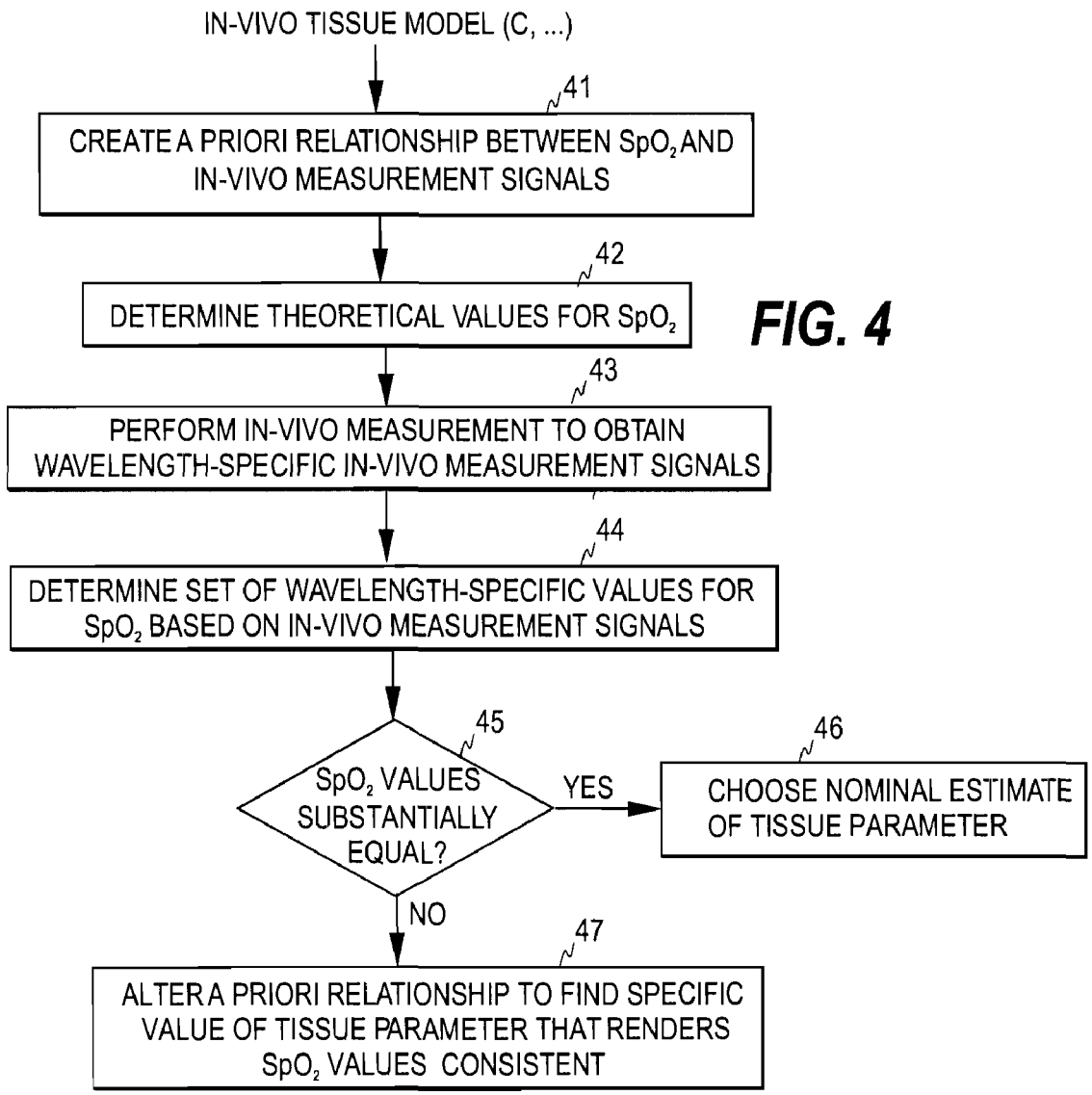
FIG. 4 is a flow diagram illustrating one embodiment of the method of FIG. 3.
Figure 6A:
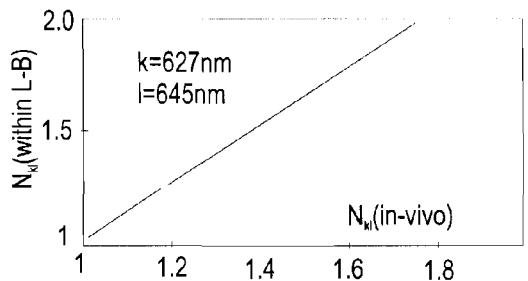
FIG. 6a to 6f illustrate examples of transformations defining the relationship between the in-vivo modulation ratio N(in-vivo) and the Lambert-Beer modulation ratio N(L-B)
Figure 6B:
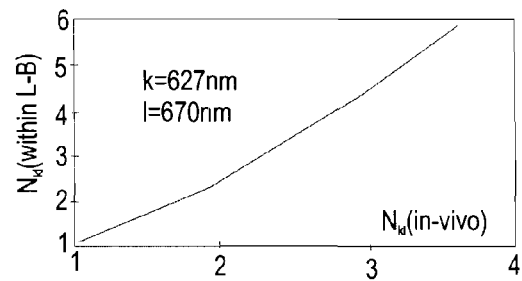
Figure 6C:
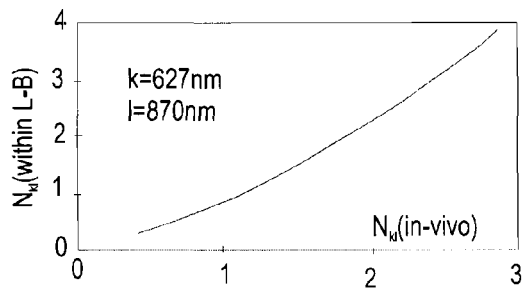
Figure 6D:
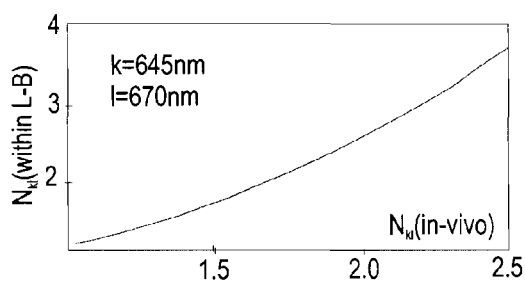
Figure 6E:
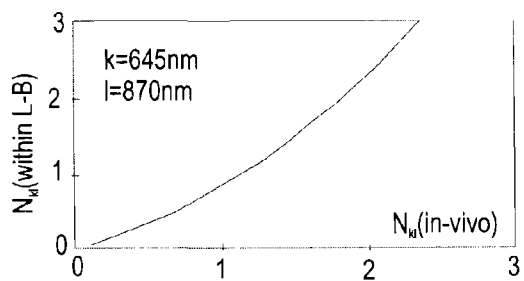
Figure 6F:
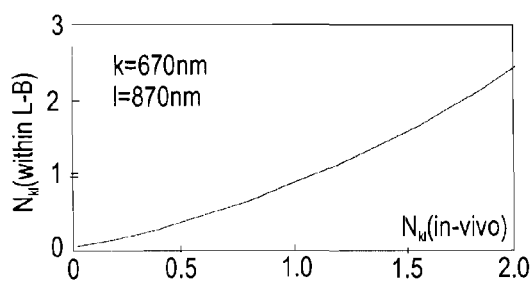
Figure 7A:
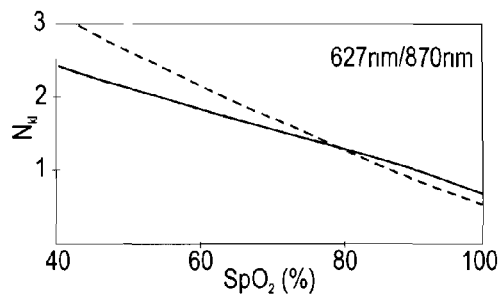
FIG. 7a to 7f illustrate the in-vivo measured and theoretical Lambert-Beer modulation ratios as a function of $SpO_2$.
Figure 7B:
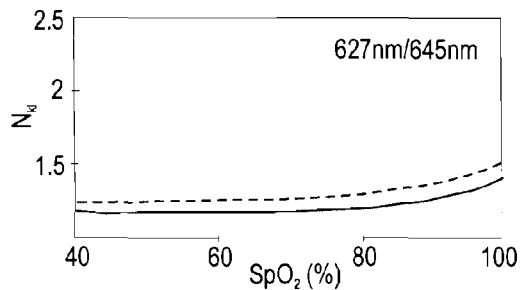
Figure 7C:
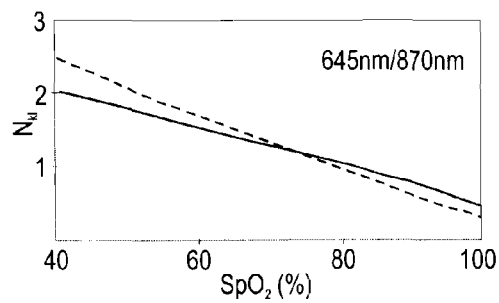
Figure 7D:
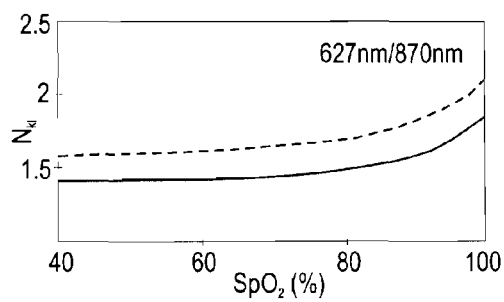
Figure 7E:
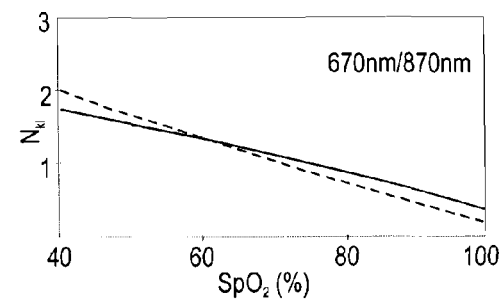
Figure 7F:
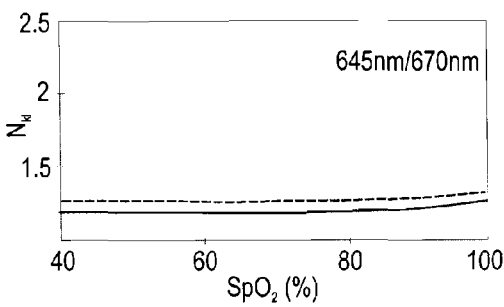
Figure 8:
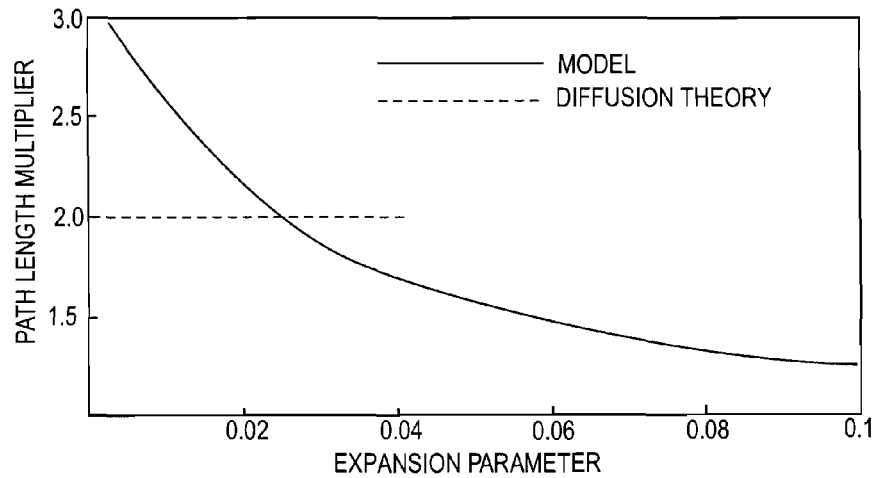
FIG. 8 illustrates the path length multiplier PLM as a function of an expansion parameter $\Sigma_a/\Sigma'_s$.

FIG. 4 illustrates an embodiment of the invention, in which the predetermined parameter represents the arterial oxygen saturation, $SpO_2$. Conventional oximeters calculate $SpO_2$ from signals measured at two wavelengths, typically, as mentioned before, at 660 nm and 940 nm. However, the oxygen saturation can as well be determined from any other two wavelengths. When more than two wavelengths are employed in a pulse oximeter, the rule of consistency is that the same saturation percentage must be obtained from any wavelength pair. For instance, if there are three wavelengths, say 650 nm, 760 nm and 880 nm, the first $SpO_2$ value can be determined from 650 nm and 760 nm, the second value from 650 nm and 880 nm, and a third estimate for $SpO_2$ from 760 nm and 880 nm. The oxygen saturation $SpO_2$, i.e. the oxyhemoglobin fraction in percentage, must be the same for all wavelength pairs. In this case an a priori relationship is thus formed between the $SpO_2$ and the in-vivo signals measured at the wavelengths of the apparatus (step 41). The a priori relationship can be such that it maps, at each wavelength pair, the ratio of measured AC/DC-signals to a $SpO_2$ value. The nominal relationships between the signal ratios and $SpO_2$, i.e. the mapping functions, may be stored in the memory of the apparatus (step 42).

In-vivo measurements are then made using several wavelength pairs (step 43) and an in-vivo based set of $SpO_2$ values is determined based on the in-vivo measurement signals and the relationships (step 44). Since $SpO_2$ values may change through time, consistency is achieved for the different wavelengths if it is detected that the in-vivo based $SpO_2$ values obtained in the measurement are essentially the same. The values are compared with each other at step 45. However, if it is detected at step 45 that the $SpO_2$ values deviate substantially from each other, inconsistency is detected. The concentration value is then sought for at step 47, which yields a minimum difference between the in-vivo based $SpO_2$ values.

The concentration value obtained corresponds to a situation in which the effect of the in-vivo tissue on the measured in-vivo signals is consistent for the wavelengths at which the $SpO_2$ values were measured. In case of $SpO_2$ being the predetermined parameter, the consistency requirement means that the arterial blood color seen against a varying background color and color density must be the same and independent of the background properties. Arterial blood thus serves as a color marker, which must be detected consistently at all wavelengths regardless of the background properties. In analogous simple terms, to an eye the color of an object seems to depend on the background against which the object is seen. However, although the object looks differently, the object's true color is the same. In this case the object is the arterial blood, the true color corresponds to the arterial saturation, SaO2, to which all other tissue components form the background.

In summary, the present invention is based on a general principle of using arterial hemoglobin (pulsating hemoglobin) as a marker, which must be seen the same independent of the background tissue. By requiring that the true color must be invariant, the properties of the background can actually be determined. The concentration of total hemoglobin or glucose or any other blood substance in the background can thus be determined using this principle. Below, the principle of the present invention is applied to the measurement of total hemoglobin.

Next, an embodiment according to FIG. 4 is discussed in more detail with reference to FIGS. 5 to 8.

$SpO_2$ within the Lambert-Beer Model

Within the L-B model, the transmitted light through the tissue layers can be expressed mathematically as follows:

$$I_{out} = I_{in} \times \exp(-\Sigma(c_i \times \epsilon_i \times l_i)), \quad (1),$$

where $I_{in}$ is the light intensity input and $I_{out}$ is the light intensity output, $c_i$ is the concentration of the color substance in layer i, $\epsilon_i$ is the extinction coefficient of the color substance in layer i, and $l_i$ is the thickness of layer i. The basic oximeter equation can be obtained by differentiating the transmitted intensity with time and remembering that the only time variant absorption is due the arterial blood, which results in:

$$AC/DC \text{ (within L-B)} = \Delta I/I = -c_a \times \epsilon_a \times I_a \quad (2),$$

where AC and DC refer to the AC and DC components of light transmission (cf. FIG. 2), $\Delta I$ refers to the pulsatile transmitted light intensity, I refers to the total transmitted light intensity, subscript a refers to arterial blood, $\epsilon_a$ refers to the extinction coefficient of the arterial blood, $c_a$ to the concentration of the substance in blood, and $I_a$ represents the thickness of the pulsating, time variant blood layer (layer 23 in FIG. 2).

In pulse oximeters, the light transmission measurement is performed at two wavelengths, red and infrared, respectively. The ratio of the AC/DC ratios at these wavelengths is in this context termed modulation ratio and denoted with $N_{kl}$, where the subscripts k and l refer to the wavelengths. The AC/DC ratio at wavelength i is denoted with dAi. Consequently, $N_{kl} = dA_k/dA_l$. By assuming a Lambert-Beer model for the absorption in arterial blood and that there are only two hemoglobin species, oxyhemoglobin and deoxyhemoglobin, in blood with respective fractions $SpO_2/100$ and $(100-SpO_2)/100$, an ideal L-B relationship is obtained:

$$SpO_{2kl} = \frac{\varepsilon_{kHb} - N_{kl} * \varepsilon_{lHb}}{N_{kl} * (\varepsilon_{lHbO2} - \varepsilon_{lHb}) - (\varepsilon_{kHbO2} - \varepsilon_{kHb})}, \quad (3)$$

where the wavelengths are denoted by k and l, $N_{kl}$ is the above modulation ratio for the wavelengths k and l, $\epsilon$ is the extinction coefficient, and HbO2 and Hb refer, respectively, to oxyhemoglobin and deoxyhemoglobin.

The Concept of a Path Length Multiplier

Figure 5:
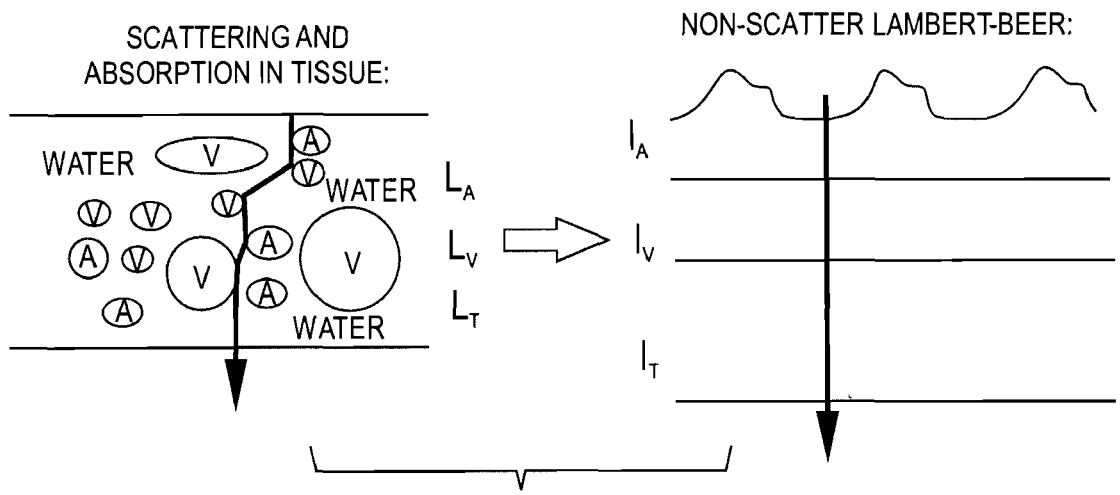
FIG. 5 illustrates the actual in-vivo and Lambert-Beer model based light transmissions in tissue.

FIG. 5 illustrates the principles of establishing the relationship between the measured in-vivo light signal and the non-scatter light signal within the L-B tissue model. Due to scattering, the actual light path through the tissue is longer than in the Lambert-Beer model. The relationship between the in-vivo measured signals and the corresponding signals within the model can be constructed by calculating, at each wavelength, a path length multiplier (PLM), which describes how much longer the actual light path through a particular tissue layer is in comparison to the ideal straight line. PLM is thus a measure for the effect of light scattering in tissue: the larger the scattering relative to absorption, the longer the actual light path length through the tissue. With constant scattering, the light path shortens as absorption increases. The calculation of PLM will be described in more detail below.

With the help of the PLM concept, the actual pulse oximeter signal can be expressed as follows:

$$AC/DC\ (\text{in-vivo}) = \Delta I/I = -c_a \times \epsilon_a \times L_a, \quad (4)$$

where $L_a$ is the real path length through the pulsating arterial blood. Using the PLM, it may then be written:

$$L_a = PLM(\lambda, \Sigma_a, \Sigma_s) \times I_a, \quad (5)$$

i.e. $L_a$ is a function of wavelength, total absorption ($\Sigma_a$), and scattering ($\Sigma_s$) of the tissue (by all tissue layers/ components).

Alternatively, the above equation may be expressed by the equation:

$$AC/DC\ (\text{in-vivo}) = \Delta I/I = -c_a \times PLM \times \epsilon_a \times I_a \quad (6)$$

which defines an in-vivo extinction coefficient $\epsilon_a$ as follows:

$$\epsilon_a = PLM(\lambda, \Sigma_a, \Sigma_s) \times \epsilon_a. \quad (7)$$

The path length multiplier PLM can thus be thought to alter either the extinction coefficients or the path lengths within the L-B theory To sum up, PLM is a function of wavelength, scattering and absorption, i.e. color and color density of the absorbing tissue layers of the background and arterial blood.

The Transformation Between the In-Vivo Signals and the Fictitious Lambert-Beer Model Signals Next, the path length multiplication concept is utilized to mathematically establish a relationship between the in-vivo measured signals and the fictitious signals in the Lambert-Beer tissue model. Using the above path length equations, the modulation ratio N can be expressed as follows:

$$N_{12} = AC/DC(\text{in-vivo}, \lambda_1)/AC/DC(\text{in-vivo}, \lambda_2) = (-c_a*\epsilon_a^1*L_a^1)/(-c_a*\epsilon_a^2*L_a^2) = (\epsilon_a^1*PLM^1*I_a^1)/(\epsilon_a^2*PLM^2*I_a^2), \quad (8)$$

where the subscripts and superscripts 1 and 2 refer to the two different wavelengths ($\lambda_1$, $\lambda_2$).

Because $I_a^1 = I_a^2$ the above equation reduces to:

$$N_{12}(\text{in-vivo}) = PLM^1/PLM^2 \times \epsilon^1/\epsilon^2 = PLM^1/PLM^2 \times N_{12} \text{ (within L-B)} \quad (9)$$

A function g is now defined as the relationship between $N_{12}$(in-vivo) and $N_{12}$(within L-B): $N_{12}$(in-vivo)=g($N_{12}$(within L-B)). The transformation from the in-vivo measured modulation ratio to the ideal fictitious modulation ratio in the L-B, can then be expressed by the inverse function $g^{-1}$ as follows:

$$N_{kl}(\text{within L-B}) = g^{-1}(k, l, \text{tissue properties}, N_{kl}(\text{in-vivo})) \quad (10),$$

where the transformation depends on the background tissue color, on the color density, and on the wavelengths k and l.

The total hemoglobin, THb, is the tissue parameter that essentially determines the color density of the background. The background color is mainly determined by the arterial and venous saturations and relative arterial and venous volume proportions.

Determination of the Transformations g

The transformations g(k,l) may be found by the following two methods:
1) Empirically by measuring N(in-vivo) and the concentrations of the different hemoglobin species in blood by a co-oximeter, and then calculating from the hemoglobin concentrations the N(within L-B) for each wavelength pair; or
2) By empirically determining the above relationship for one wavelength pair (optimally 660 nm and 940 nm) and then extrapolating the relationship to other wavelength pairs by using a wavelength dependent tissue model.

Though the method 1) is possible, it requires a considerable amount of work, because the relationships, such as those in FIGS. 6a to 6f, must be determined for each free tissue parameter, for instance THb, separately. Furthermore, the background tissue properties change the transformations only slightly, and the changes may be masked by the inaccuracies of the measurement itself. Another difficulty is to maintain background properties that are constant enough in a dynamical clinical or laboratory test situation.

Therefore, the above method 2) is used in this context. Examples of transformations g obtained by this method for nominal a priori tissue parameter values are shown in FIG. 6a to 6f, which illustrate the transformations for the wavelengths of 627, 645, 670, and 870 nm.

The transformations between the Lambert-Beer model and in-vivo measurements are also discussed in U.S. Pat. No. 6,104,938.

The transformations can be presented also as second order polynomies. Table 1 summarizes these polynomies for the above 627-645-670-870 nm pulse oximetry.

TABLE 1

| N(within L-B) = a × [N(in-vivo)]$^2$ + b × N(in-vivo) + c; | | | |
|---|---|---|---|
| Wavelengths (nm) | a | b | c |
| 627,870 | 0 | 1.323 | −0.320 |
| 645,870 | 0 | 1.317 | −0.307 |
| 670,870 | 0.251 | 0.671 | −0.020 |
| 627,670 | 0.635 | −0.376 | 0.785 |
| 645,670 | 0.311 | 0.589 | −0.008 |
| 627,645 | 0.361 | 0.512 | 0.023 |

The Extrapolation of the Standard Oximetry R-Calibration to Other Wavelengths Using an In-Vivo Tissue Model The transformation g at 660 nm/940 nm, i.e. at the wavelengths of a standard pulse oximeter, is the mapping function from the N-ratio(within L-B) to the N-ratio(in-vivo). This particular transformation can be determined accurately because the empirical relationship is based on thousands of blood samples used to calibrate conventional pulse oximeters operating at the said wavelengths. Therefore, this N-ratio relationship, i.e. function g(660 nm, 940 nm), is first used to establish a realistic tissue model, which will eventually reproduce the calibration for the 660 and 940 nm pulse oximeter. The tissue model is developed with a number of tissue parameters that first assume typical nominal values reflecting the average tissue conditions at the device calibration set-up. One of the model parameters included is the wavelength. Once a satisfactory model with nominal tissue properties is found for the 660-940 nm oximetry, the wavelength dependence is used to extrapolate the in-vivo signals vs. $SpO_2$ relationships for other wavelength pairs.

FIG. 7a to 7f represent the in-vivo measured and theoretical Lambert-Beer modulation ratios as a function of $SpO_2$ for the wavelengths of Table 1. Solid lines represent in-vivo values, while dashed lines represent Lambert-Beer values.

The Parameterized In-Vivo Tissue Model

Using the Monte-Carlo type numeric tissue modeling or other more conventional tissue models, it has been shown that the higher the scattering in the tissue, the longer the actual light path length through the tissue. Furthermore, increased absorption with constant scattering decreases the path length through the tissue. It is therefore reasonable to estimate the actual in-vivo path length using the ratio of the tissue absorption and scattering efficiencies as a parameter in a series expansion of the path length. The series expansion, such as Taylor series expansion, may be derived relative to a very highly scattering medium, i.e. relative to predictions of the diffusion approximation with $\Sigma_a/\Sigma_s=0$. As a result, the path length multiplier PLM may be expressed as follows:

$$PLM = D - B \times (D-1) \times (\Sigma_a/\Sigma'_s) + (A/2) \times B \times (B-1) \times (D-1) \times (\Sigma_a/\Sigma'_s)^2 \quad (11)$$

where A, B, and D are series expansion coefficients and $$\frac{\Sigma_a}{\Sigma'_s}(\lambda) = \frac{\Sigma_a}{\Sigma'_s}(\lambda_0) \times \left(\frac{\lambda}{\lambda_0}\right)^N \times \frac{\Sigma_a(\lambda)}{\Sigma_a(\lambda_0)} \quad (12)$$

$$= \left((1 - bvf) \times C_{tissue} + bvf \times \frac{THb}{THb_N} \times \frac{(1-H_N) \times (1.4 - H_N)}{(1-H) \times (1.4 - H)}\right) \times \left(\frac{\lambda}{\lambda_0}\right)^n \times$$

$$\frac{bvf \times (f_a \times \mu_a(\lambda) + f_v \times \mu_v(\lambda)) + wf \times \mu_w(\lambda)}{bvf \times (f_a \times \mu_a(\lambda_0) + f_v \times \mu_v(\lambda_0)) + wf \times \mu_w(\lambda_0)}$$

where bvf is the blood volume fraction; wf is the water volume fraction; $\mu_a$, $\mu_v$ and $\mu_w$ are, respectively, the arterial, venous and water linear absorption coefficients; tHb and H refer respectively to total hemoglobin and hematocrit; fa and fv are the arterial and venous blood volume fractions; $\lambda$ is the wavelength; $\lambda_0$ is the isobestic (805 nm) wavelength for oxy- and reduced hemoglobin; and the subscript N refers to the nominal value of the respective parameter.

The tissue parameters with their nominal values are summarized in Table 2 below.

TABLE 2

| | | Empirical Range | Nominal value |
|---|---|---|---|
| Model parameters | D | >1 | 3.2 |
| | B | NA | 30 |
| | A | <=1 | 0.75 |
| Tissue parameters | $\Sigma_a/\Sigma'_s$ for bloodless tissue ($C_{tissue}$) | 0.01-0.02 | 0.02 |
| | Wf | 0.6-0.9 | 0.75 |
| | Bvf | 0.01-0.1 | 0.025 |
| | Exponent for wavelength dependent scattering [N] | 0.4-2 | 0.4 (900 nm); 0.9 (660 nm) |
| Blood parameters | $THb/THb_0$ | 0.5-1.5 | 1 |
| | H | 0.25-0.5 | 0.45 |
| | $\Sigma_a/\Sigma'_s$ for whole blood at 805 nm ($C_{blood}$) | 0.1-0.2 | 0.2 |
| | DysHb | 0.01-0.03 | 0.015 |
| | Fa | 0.2-0.4 | 0.25 |
| | Difference of the venous and arterial saturation (Vena-Artdiff) | 5-30% | 10% |

The expression for the term $(\Sigma_a/\Sigma'_s)$ (Eq. 12), termed expansion parameter in this context, is here determined by utilizing Lambert-Beer compartment model for $\Sigma_a$ and taking the tissue parameter values from the empirical tissue data available in literature (Table 2).

Next, the series expansion coefficients A, B, and D are determined by fitting them so that they reproduce the transformation function g for the conventional 660/940 nm pulse oximeter. The PLM so obtained is presented as a function of the expansion parameter $(\Sigma_a/\Sigma'_s)$ in FIG. 8. Once the expansion coefficients A, B and D are known, the ratio of the two PLM's (Eq. 11, 12) is calculated at any two desired wavelengths. This ratio determines the transformations g(k,l) (Eq. 10), hereafter termed FRactional OXimetry (FROX) transformation.

Determination of Hemoglobin Using the FROX Transformation and $SpO_2$

For the given transformations g(k,l) the $SpO_2$ can be obtained from the in-vivo measured N ratios using the equation:

$$SpO_2(k, l) = \frac{\varepsilon_{kHb} - g_{kl}^{-1}(THb) \times N_{kl}^{in-vivo} \times \varepsilon_{lHb}}{g_{kl}^{-1}(THb) \times N_{kl}^{in-vivo} \times (\varepsilon_{lHbO2} - \varepsilon_{lHb}) - (\varepsilon_{kHbO2} - \varepsilon_{kHb})} \quad (13)$$

where N(in-vivo) is denoted with $N^{in-vivo}$. This equation represents the a priori relationship between $SpO_2$ and in-vivo measurement signals, cf. step 31 and 41. As discussed below, the equation may be stored either in the sensor or in the processing unit of the pulse oximeter.

If the blood contains only two hemoglobin species, oxyhemoglobin (HbO2) and reduced hemoglobin (Hb), the $SpO_2$ calculated at any two wavelengths must result in the same value. The measurement of hemoglobin can now be based on the PLM model (Eq. 9-12) in which the hemoglobin concentration, THb and H, is adjusted so that all $SpO_2(k,l)$ values calculated according to Equation (13) are essentially the same.

Hemoglobin measurement requires a minimum of three wavelengths (1, 2, 3). $SpO_2$ may, in this case, be calculated in two independent ways: from $N_{12}$ and $N_{13}$. $N_{23}$ may be calculated from these two as the ratio $N_{13}/N_{12}$. Therefore, $SpO_2(2, 3)$ is not independent as it may be derived from $SpO_2(1,2)$ and $SpO_2(1,3)$. The use of three wavelengths thus allows the determination of the $SpO_2$ value and one dominating tissue parameter, i.e. THb. The accuracy of THb may be improved by using more wavelengths: with four wavelengths, three independent $SpO_2$ values may be calculated. This results in an estimate of a true $SpO_2$ and two free tissue parameters, such as THb and venous saturation. In one embodiment of the present invention, 6 to 8 wavelengths are used, which allows the determination of all important tissue parameters through, respectively, 5 to 7 independent $SpO_2$ equations. In general, M-2 tissue parameters may be determined based on M wavelengths. It is assumed here that oxyhemoglobin and deoxyhemoglobin (reduced hemoglobin) are the only color components in blood. In presence of dyshemoglobins, more wavelengths are needed to estimate the tissue parameters. For instance, with both methemoglobin (metHb) and carboxyhemoglobin (HbCO) in blood, a minimum of 5 wavelengths are needed for the determination of THb. In this case, it is required that for each possible combination of 4 wavelengths, the same fractional hemoglobin composition shall be obtained.

Above, the predetermined parameter that is employed to detect consistency is the color of arterial blood, that is $SpO_2$ or the fractions of a predetermined hemoglobin component. This embodiment of the present invention may be summarized so that in the absence of dyshemoglobins a set of M-1 values of the predetermined parameter, i.e. $SpO_2(k,I)$, may be calculated based on signals at M wavelengths. The tissue model, including THb as a tissue parameter, is adjusted to search for the THb values that renders $SpO_2(k,I)$ values the same.

Above, the embodiment utilizing $SpO_2$ as the predetermined parameter was discussed in more detail. Below, a second embodiment of the invention is discussed with reference to FIG. 9. The second embodiment is based on isobestic signals and pseudo-isobestic invariants.

Figure 9:
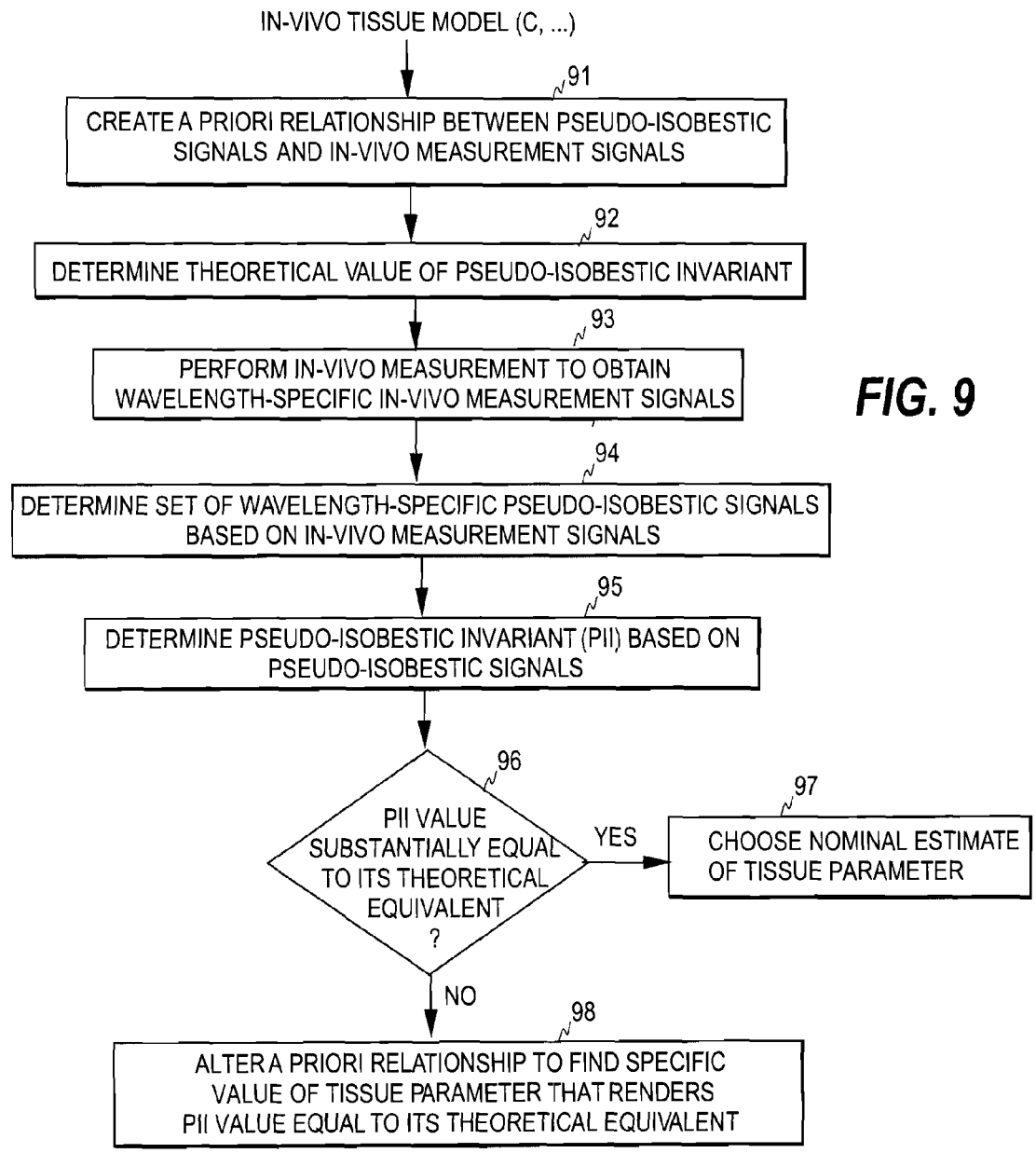
FIG. 9 is a low diagram illustrating a further embodiment of the method of FIG. 3.

FIG. 9 illustrates an embodiment of the invention, in which the predetermined parameter is an isobestic signal. An isobestic signal here refers to a weighted sum of two signals, the weight being selected so that the sum signal is isobestic, i.e. independent of the relative concentrations of the hemoglobin species. In case of an isobestic signal being the parameter reflecting the effect of the tissue on the useful signal, consistency is achieved for the different wavelengths if a quotient of two pseudo-isobestic signals is essentially the same as its theoretical equivalent. The quotient, which is theoretically a constant parameter, is in this context termed pseudo-isobestic invariant (PII). Pseudo-isobestic signals and invariants are discussed in the above-referred U.S. Pat. No. 6,501,974.

Determination of Hemoglobin Using the FROX Transformation and Pseudo-Isobestic Signals In this embodiment of the invention, the a priori relationship is thus formed between in-vivo and pseudo-isobestic signals (step 91) and the theoretical value of PII is determined and stored in the apparatus (step 92). Steps 91 and 92 are carried out in the manufacturing phase of the apparatus.

After this, when the apparatus is in use, the in-vivo measurements are made by measuring the transmission signals at three or more wavelengths and at least one in-vivo based value is determined for the PII based on the in-vivo measurement signals and the relationship (step 93-95). The said at least one value is compared with the stored theoretical value of PII (step 96). If the obtained value(s) is/are substantially the same as the theoretical value, the effect of the background on the measurement signal is substantially consistent at the different wavelengths, and the a priori assumption may be regarded as correct (step 97).

However, typically there is a substantial difference between the theoretical value and the in-vivo based value(s) obtained at step 95. The a priori relationship is then altered to find out the concentration value for which the obtained PII value(s) correspond, as accurately as possible, the theoretical value of the PII (step 98).

Below, an embodiment according to FIG. 9 is discussed in more detail.

A photon hitting the detector at each wavelength must cross the same thickness or the same number of Hb molecules of pulsating arterial blood in the L-B tissue model. In other words, $c_a \times I_a$, i.e. the product of the hemoglobin concentration and blood volume thickness, is an invariant. As can be seen from equation (1), the L-B modulation ratio AC/DC (within L-B) is proportional to this invariant, the proportionality coefficient being the extinction coefficient of pulsating arterial blood. Next, a new set of equations is constructed so that other estimates for the tissue model parameters may be determined.

Pseudo-Isobestic Invariant, PII

'The color' is first eliminated from the signals. The color is an invariant in the SpO2 parameter; optimally the new set of parameters can best complement the color invariant, if the color is eliminated from the set of new equations. At the isobestic point of oxyhemoglobin and deoxyhemoglobin the signal does not depend on the relative proportions of the hemoglobin fractions, i.e. the signal is color invariant. A color invariant signal may be calculated from two color dependent signals by summing the signals in the proportions that lead to invariancy. The resulting signal (within L-B), which is called pseudo-isobestic signal, may then be defined in the following way:

$$S(k,I) = dA_k + f_{k,l} \times dA_l = dA \times (\epsilon_k^{RHb} + f_{k,l} \times \epsilon_l^{RHb}) \quad (14)$$

where $$f_{k,l} = \frac{\varepsilon_k^{RHb} - \varepsilon_k^{HbO2}}{\varepsilon_l^{RHb} - \varepsilon_l^{HbO2}}$$

and dA is a common factor proportional to $c_a * I_a$, i.e. to the number of hemoglobin molecules in the pulsating arterial blood.

The pseudo isobestic invariant within L-B is the ratio of two pseudo-isobestic signals. This ratio is independent of both the color, the volume, and the THb of blood. The pseudo isobestic invariant PII may be written in the following way:

$$PII(k, l, m, n) = \frac{dA \times (\varepsilon_k^{RHb} + f_{k,l} \times \varepsilon_l^{RHb})}{dA \times (\varepsilon_m^{RHb} + f_{m,n} \times \varepsilon_n^{RHb})} \quad (15)$$

Using the actual in-vivo measured signals, PII can be written as follows:

$$PII(k, l, m, n) = \frac{dA_k + f_{k,l} \times dA_l}{dA_m + f_{m,n} \times dA_n}$$

$$= \frac{dA_l}{dA_n} \times \frac{\frac{dA_k}{dA_l} + f_{k,l}}{\frac{dA_m}{dA_n} + f_{m,n}}$$

$$= N_{ln}^{L-B} \times \frac{N_{kl}^{L-B} + f_{k,l}}{N_{mn}^{L-B} + f_{m,n}}$$

$$= g_{ln}^{-1}\left(N_{ln}^{in\text{-}vivo}\right) \times \frac{g_{kl}^{-1}\left(N_{kl}^{in\text{-}vivo}\right) + f_{k,l}}{g_{mn}^{-1}\left(N_{mn}^{in\text{-}vivo}\right) + f_{m,n}}$$

where N(in-vivo) and N(within L-B) are denoted respectively with $N^{in\text{-}vivo}$ and $N^{L\text{-}B}$. At least three wavelengths are needed to calculate a PII from the measured signals. For 4 wavelengths 2 independent PII's (total 15 PII's) can be calculated: For M wavelengths M-2 independent PII's can be calculated. Each PII within L-B is a constant, and in principle independent of blood color ($SpO_2$) or color density (blood volume and THb). However, if the transformation g is not correct in Eq. 10, the value of PII determined based on the measured signals may differ from its theoretical constant value. The total hemoglobin THb and other parameters in the tissue model can now be adjusted so that the predetermined theoretical PII values are obtained. The tissue model parameters that render the PII invariant determine the total hemoglobin THb in blood.

The above two embodiments, in which the predetermined parameter is, respectively, $SpO_2$ or PII, may also be combined so that both $SpO_2$ and PII are employed. This method may be summarized as follows:

An in-vivo tissue model is first constructed. Within this model an expression for the path length multiplier is defined at each wavelength.

- 6-8 wavelengths are selected and pulse oximeter measurement is performed at all wavelengths.
- The transformations g from the measured in-vivo N-ratio to the theoretical L-B N-ratio is calculated for each wavelength pair. Nominal tissue parameter values are used for the nominal g functions.
- A first predetermined parameter, $SpO_2$, is calculated using the nominal transformations. M-1 different and independent $SpO_2$ values can be determined for M different wavelengths.
- A second predetermined parameter, PII, is calculated using all wavelength signals. N-2 different and independent PII's can be calculated.
- The functions g are altered by altering the tissue model parameters, including THb and H, until:
  1. The calculated $SpO_2$ values are all the same or almost the same,
  2. the calculated PII's match or almost match with their theoretical constant values.
- Finally, the THb and H, which produce the closest agreement with the measured signals and the predetermined invariants, are the desired hemoglobin concentration and the hematocrit value.

Figure 10:
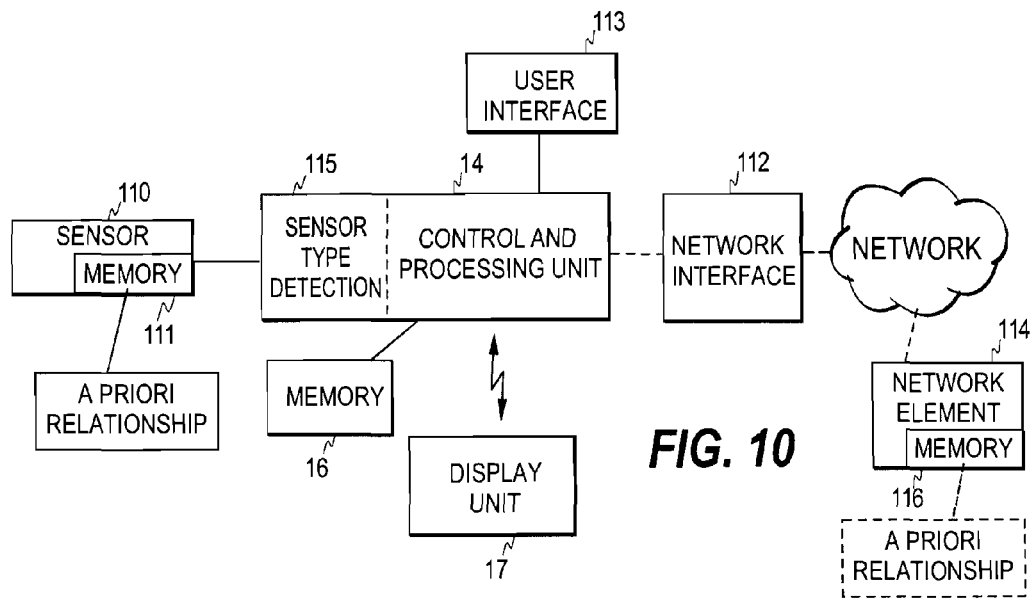
FIG. 10 illustrates one embodiment of the apparatus of the invention.

The pulse oximeter of FIG. 1 includes an algorithm 18 carrying out the above steps. Furthermore, the a priori relationship is stored in the memory of the pulse oximeter in the manufacturing phase of the apparatus. However, it is to be noted that that all the operations of the invention are not necessarily carried out in the actual pulse oximeter or in its control and processing unit, but the entities carrying out the operations of the invention may be distributed between the sensor attached to the patient, the actual pulse oximeter device, i.e. the central unit, and/or a communication network. For example, the a priori relationship may be stored in any of these locations. Furthermore, the elements that determine the value of the tissue parameter yielding consistency may be distributed between one or more of these possible locations. For example, the storing of the a priori relationship and the determination of the said value may take place in various processing units of a network, such as the local area network of a hospital. FIG. 10 illustrates an example of an apparatus in which the a priori relationship is stored in the memory 111 of a sensor 110 attachable to the patient, whereas the data processing entities are in the central unit 14 of the pulse oximeter. Furthermore, in this example, the connection between the central unit and the monitor is wireless. Any appropriate short-range wireless radio technology may be used to transfer the data from the central unit to the monitor.

The pulse oximeter may also be provided with a network interface 112 for downloading/updating the a priori relationship through a network from a network element 114 storing the a priori relationship. This is illustrated with dotted lines in the figure.

In one embodiment of the invention, the central unit is compatible with both a conventional sensor (two wavelengths) and an advanced sensor according to the invention (three or more wavelengths and optional data for the determination of the concentration). The central unit may be provided with a recognition module 115 for recognizing the type of the sensor. If the recognition module detects that an advanced sensor according to the invention is connected to it, it may download data from the sensor and/or network according to the parameters to be displayed. The advanced oximeter of the invention may display the hemoglobin concentration and dyshemoglobin fractions together with fractional or functional oxyhemoglobin percentages. The user of the device may configure the parameters to be displayed through a user interface 113.

A pulse oximeter may also be upgraded to a device capable of determining the concentration of a substance in the blood of a patient. Such an upgrade may be implemented by delivering to the pulse oximeter a software module that enables the device to carry out the above steps. The software module may be delivered, for example, on a data carrier, such as a CD or a memory card, or through a telecommunications network. The software module may be provided with a memory holding the a priori relationship and/or with access to an external memory holding the a priori relationship.

Although the invention was described above with reference to the examples shown in the appended drawings, it is obvious that the invention is not limited to these, but may be modified by those skilled in the art without departing from the scope and spirit of the invention.

The invention claimed is:

1. A method for determining concentration of a substance in blood of a subject, the method comprising:
    creating an a priori relationship indicative of the effect of tissue on in-vivo measurement signals at at least three wavelengths, wherein the in-vivo measurement signals are indicative of absorption caused by blood of a subject;
    acquiring the in-vivo measurement signals from in-vivo tissue at the at least three wavelengths;
    determining, based on the a priori relationship, a specific value of a tissue parameter for which the effect of the in-vivo tissue on the in-vivo measurement signals is consistent for the at least three wavelengths, the specific value representing concentration of the substance in the blood of the subject; and
    presenting the specific value as the determined concentration of the substance in blood of the subject.

2. The method according to claim 1, wherein the creating includes creating the a priori relationship through an in-vivo tissue model including a nominal estimate of the tissue parameter.

3. The method according to claim 2, wherein
the creating includes creating the a priori relationship, in which the a priori relationship defines a predetermined parameter as a function of the in-vivo measurement signals; and
the determining includes (i) defining a set of wavelength-specific values for the predetermined parameter and (ii) finding out the specific value of the tissue parameter, wherein the specific value renders the set of wavelength-specific values consistent.

4. The method according to claim 3, wherein the finding out includes conditionally altering the a priori relationship determine the specific value of the tissue parameter that renders the set of wavelength-specific values consistent.

5. The method according to claim 4, wherein the creating includes creating the a priori relationship, in which the predetermined parameter represents one of arterial oxygen saturation (SpO2), fractional composition of a plurality of hemoglobin species in the blood of the subject, and a pseudo-isobestic signal.

6. The method according to claim 5, wherein the creating includes creating the a priori relationship, in which the predetermined parameter represents arterial oxygen saturation (SpO2); and
a condition upon which the altering is conditional is whether the difference between the wavelength-specific values within the set is greater than a predetermined threshold, such that the altering is performed when the difference between the wavelength-specific values within the set is greater than the predetermined threshold and the altering is not performed when the difference between the wavelength-specific values within the set is not greater than the predetermined threshold.

7. The method according to claim 6, wherein the finding out includes selecting the nominal estimate as the specific value when the altering is not performed.

8. The method according to claim 4, wherein the creating includes creating the a priori relationship, in which the predetermined parameter represents a pseudo-isobestic signal; and
a condition upon which the altering is conditional is whether a quotient of two pseudo-isobestic signals is substantially the same as its theoretical equivalent, such that the altering is performed when the quotient is not substantially the same as its theoretical equivalent and the altering is not performed when the quotient is substantially the same as its theoretical equivalent.

9. An arrangement for determining concentration of a substance in blood of a subject, the arrangement comprising:
a first determination unit configured to store an a priori relationship indicative of the effect of tissue on in-vivo measurement signals at at least three wavelengths, wherein the in-vivo measurement signals are indicative of absorption caused by blood of a subject;
a measurement unit configured to acquire the in-vivo measurement signals from in-vivo tissue at the at least three wavelengths;
a second determination unit configured to determine, based on the a priori relationship, a specific value of a tissue parameter for which the effect of the in-vivo tissue on the in-vivo measurement signals is consistent for the at least three wavelengths, the specific value representing concentration of a substance in the blood of the subject; and
a display unit for presenting the specific value as the determined concentration of the substance in blood of the subject.

10. The arrangement according to claim 9, wherein the a priori relationship is created through an in-vivo tissue model including a nominal estimate of the tissue parameter.

11. The arrangement according to claim 10, wherein the first determination unit is configured to store the a priori relationship, in which the a priori relationship defines a predetermined parameter as a function of the in-vivo measurement signals; and
the second determination unit is configured to (i) define a set of wavelength-specific values for the predetermined parameter and (ii) find out the specific value of the tissue parameter, wherein the specific value renders the set of wavelength-specific values consistent.

12. The arrangement according to claim 11, wherein the second determination unit is further configured to conditionally alter the a priori relationship to determine the specific value of the tissue parameter that renders the set of wavelength-specific values consistent.

13. The arrangement according to claim 12, wherein the predetermined parameter represents one of arterial oxygen saturation (SpO2), fractional composition of a plurality of hemoglobin species in arterial blood, and a pseudo-isobestic signal.

14. The arrangement according to claim 13, wherein
the predetermined parameter represents a pseudo-isobestic signal; and
the second determination unit is configured alter the a priori relationship when a quotient of two pseudo-isobestic signals fails to be substantially the same as its theoretical equivalent and not to alter the a priori relationship when the quotient is substantially the same as its theoretical equivalent.

15. The arrangement according to claim 12, wherein the second determination unit is configured to alter the a priori relationship when a difference between the wavelength-specific values within the set is greater than a predetermined threshold and not to alter the a priori relationship when the difference fails to be greater than the predetermined threshold.

16. The arrangement according to claim 9, wherein the first determination unit, the measurement unit, and the second determination unit reside in a single patient monitoring device.

17. An apparatus for determining concentration of a substance in blood of a subject, the apparatus comprising:
an interface unit configured to download an a priori relationship indicative of the effect of tissue on in-vivo measurement signals at at least three wavelengths, wherein the in-vivo measurement signals are indicative of absorption caused by blood of a subject;
a signal reception unit configured to receive in-vivo measurement signals acquired from in-vivo tissue at the at least three wavelengths; and
a determination unit configured to determine, based on the a priori relationship, a specific value of a tissue parameter for which the effect of the in-vivo tissue on the in-vivo measurement signals is consistent for the at least three wavelengths, the specific value representing concentration of a substance in the blood of the subject.

18. A non-transitory computer program product embodied on a tangible medium of expression for determining concentration of a substance in blood of a subject, the computer program product comprising:
a first program product portion configured to receive an a priori relationship indicative of the effect of tissue on in-vivo measurement signals at at least three wavelengths, wherein the in-vivo measurement signals are indicative of absorption caused by blood of a subject;

a second program product portion configured to receive in-vivo measurement signals acquired from in-vivo tissue at the at least three wavelengths; and a third program product portion configured to determine, based on the a priori relationship, a specific value of a tissue parameter for which the effect of the in-vivo tissue on in-vivo measurement signals is consistent for the at least three wavelengths, the specific value representing concentration of a substance in the blood of the subject.

* * * * *